United States Patent
Cao et al.

(10) Patent No.: US 7,625,343 B2
(45) Date of Patent: Dec. 1, 2009

(54) CONCAVE PHASED ARRAY IMAGING CATHETER

(75) Inventors: Pei Jei Cao, Fremont, CA (US); Jian R. Yuan, Hayward, CA (US); Michael J. Tierney, Pleasanton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 510 days.

(21) Appl. No.: 11/173,550

(22) Filed: Jul. 1, 2005

(65) Prior Publication Data

US 2007/0016055 A1    Jan. 18, 2007

(51) Int. Cl.
*A61B 8/14* (2006.01)
(52) U.S. Cl. ........................... 600/466; 600/459
(58) Field of Classification Search .................. 600/466
See application file for complete search history.

(56) References Cited

U.S. PATENT DOCUMENTS

| | | | |
|---|---|---|---|
| 5,321,501 A | 6/1994 | Swanson et al. | |
| 5,325,860 A | 7/1994 | Seward et al. | |
| 5,368,035 A | 11/1994 | Hamm et al. | |
| 5,415,175 A | 5/1995 | Hanafy et al. | |
| 5,522,393 A | 6/1996 | Phillips | |
| 5,779,643 A | 7/1998 | Lum et al. | |
| 5,895,356 A | 4/1999 | Andrus et al. | |
| 6,102,860 A | 8/2000 | Mooney | |
| 6,120,454 A | 9/2000 | Suorsa et al. | |
| 6,485,413 B1 | 11/2002 | Boppart | |
| 6,719,694 B2 | 4/2004 | Weng et al. | |
| 6,860,856 B2 | 3/2005 | Ward et al. | |
| 2003/0032898 A1* | 2/2003 | Makin et al. | 601/2 |
| 2003/0055308 A1* | 3/2003 | Friemel et al. | 600/15 |
| 2003/0114744 A1* | 6/2003 | Pantages et al. | 600/407 |
| 2003/0236443 A1* | 12/2003 | Cespedes et al. | 600/29 |
| 2004/0068191 A1 | 4/2004 | Seward | |
| 2004/0133105 A1* | 7/2004 | Ostrovsky et al. | 600/437 |

FOREIGN PATENT DOCUMENTS

| | | |
|---|---|---|
| WO | WO 00/19908 A | 4/2000 |
| WO | WO 01/45550 A2 | 6/2001 |

OTHER PUBLICATIONS

Pompei F. Joseph et al: "Phased Array Element Shapes For Suppressing Grating Lobes" Journal of the Acoustical Society of America, AIP/Acoustical Society of America, Melville, NY, US, vol. 111, No. 5, May 2002, pp. 2040-2048.
Xie H. et al: "Endoscopic Optical Coherence Tomographic Imaging With a CMOS-MEMS Micromirror" Sensors and Actuators A, Elsevier Sequoia S.A., Lausanne, CH, vol. 103, No. 1-2, Jan. 15, 2003, pp. 237-241.
Huang et al., "Optical Coherence Tomography," Science, 254, Nov. 22, 1991, pp. 1178-1181.

* cited by examiner

*Primary Examiner*—Long V Le
*Assistant Examiner*—Saurel J Selkin
(74) *Attorney, Agent, or Firm*—Darby & Darby P.C.; Patrick R. Turner

(57) ABSTRACT

The present invention generally relates to medical devices, and more particularly to an improved intravascular device. In one embodiment, an intravascular device includes a catheter having proximal and distal portions, and a phased array of imaging elements, having edge elements each having angles of emission, located in the distal portion of the catheter, wherein the phased array is concaved having a radius of curvature such that when the phased array is steered in a maximal azimuthal direction, the angles of emission of the edge elements are substantially similar.

22 Claims, 2 Drawing Sheets

CONCAVE PHASED ARRAY IMAGING CATHETER

FIELD OF THE INVENTION

The field of the invention relates to medical devices, and more particularly to phased array imaging catheters.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

An imaging transducer generally includes an imaging element configured to emit energy pulses. During operation, the imaging element is electrically excited, thus causing an energy pulse to be emitted. The pulse is directed to a surface where imaging is desired and reflected back to the transducer. Two desirable features of the emitted energy pulse are that the energy pulse be focused and steerable. One known approach known in the art to obtain these features is to utilize an array of imaging elements instead of just one element. FIG. 1 shows an array 10 of two imaging elements, A and B, side-by-side. As is known in the art, if both elements, A and B, are excited simultaneously, then the energy pulses are combined to form a beam that is parallel to the direction that the elements, A and B, are facing, so that the beam travels directly away from the array 10. However, if a linear timing excitation gradient (a time delay based on a coherence theory) is used across the array 10, the beam can be steered in the azimuthal direction. By sending a short acoustic pulse and receiving the echo at each azimuthal direction, the array 10 may scan a sector area and construct an image. The image resolution is primarily determined by the beam 20 width in the lateral direction and the acoustic pulse length in the axial direction.

To focus the beam, i.e., adjust the beam width, time delays for each element may also be utilized. At a certain spatial location, the acoustic pulses from all elements may be coherently enhanced when they are in phase. The phase of the pulse is determined by the distance from the element to the destination location. To focus the beam at a spatial point, appropriate time delays are applied to all of the elements, A and B. These compensating delays ensure that the arrival of the acoustic pulses from different elements, A and B, are in coincidence at the desired spatial location.

The array of imaging elements configured to enable a beam to be focused and steered is known in the art as a "phased array." Though only two imaging elements, A and B, are shown in FIG. 1, a typical phased array may include as many as 256 elements. In the case of ultrasound imaging elements, each element, A and B, is generally small enough to be treated as an acoustic point source that generates a propagating wave with a spherical front. Collectively, the elements, A and B, form an acoustic field that can be enhanced when the elements, A and B, are in phase at a certain spatial location.

The elements, A and B, are typically rectangular and are typically evenly spaced across a flat plane. For ultrasound elements, each element has a pitch size equal to half a wavelength at the working ultrasound frequency. The pitch size is defined as the distance between two adjacent element, A and B, centers. With this typical configuration, when the beam 20 is steered and focused to a particular point F, the beams of the individual elements, A and B, are emitted at different angles, $\alpha$ and $\beta$, with respect to the flat plane. This will cause the beams of the individual elements, A and B, to have different amplitudes, which can undesirably result in a widened beam 20, even if an accurate time delay compensation is used. This is particularly so when the beam 20 is steered to the maximum azimuthal direction. Accordingly, an improved phased array imaging catheter would be desirable.

SUMMARY OF THE INVENTION

The present invention generally relates to medical devices, and more particularly to an improved intravascular device. In one embodiment, an intravascular device includes a catheter having proximal and distal portions, and a phased array of imaging elements located in the distal portion of the catheter, wherein the phased array is concaved.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

As described above, prior art phased array assemblies 10 consist of a series of small rectangular elements, A and B, that are evenly spaced in a flat plane. This configuration causes the elements to emit energy beams at different angles when the phased array beam 20 is steered and focused. This can undesirably cause a widened phased array beam 20.

Figure 1:
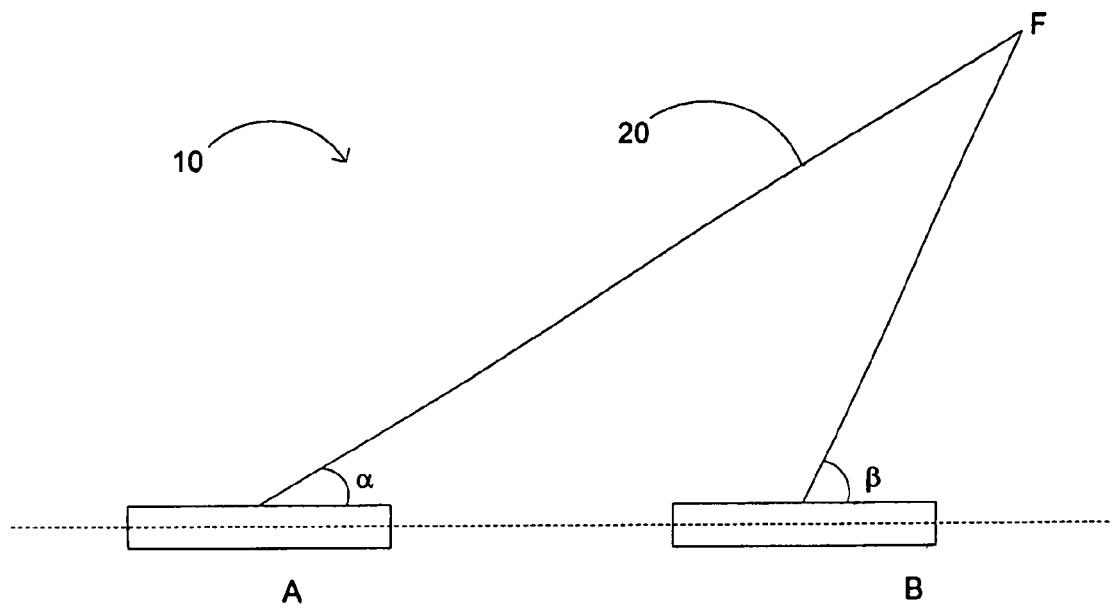
FIG. 1 is a cross-sectional side view of a phased array of imaging transducers known in the art.
Figure 2:
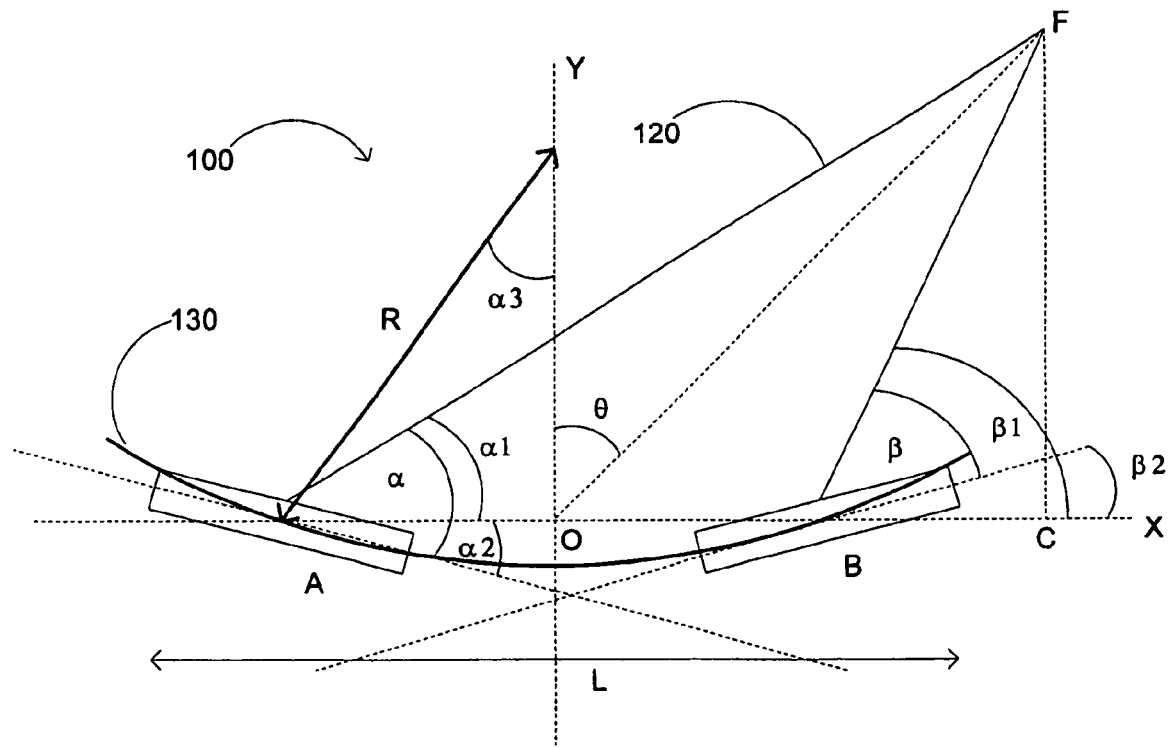
FIG. 2 is a cross-sectional side view of a phased array of imaging transducers in accordance with a preferred embodiment of the present invention.

By contrast, the improved phased array in this patent specification reduces the undesired wideness by placing a phased array in a concaved configuration, as shown in FIG. 2. FIG. 2 shows a phased array 100 of imaging elements, A and B. The elements, A and B, are situated along a concave 130 path having a radius R. The phased array 100 can have additional imaging elements along the concave path 130 (not shown). The phased array 100 has a length, L, and a maximum steering angle in the azimuthal direction, θ. F represents a focal point at the maximum steering angle in the azimuthal direction. The phased array 100 is shown focusing an energy beam, such as an acoustic pulse, 120 at focal point F. α and β, represent the tangential angles for elements A and B to the focal point F respectively. α1 and β1, represent the flat plane angles for elements A and B to the focal point F respectively. Point O represents the origin of the horizontal and vertical axis, X and Y.

In the case of a phased array 100 having a large number of imaging elements, wherein elements A and B represent the edge elements of the array 100, at focal point F, element B will have the largest angle β1, to the focal point F, whereas element A will have the smallest angle α1, to the focal point F. The concaving of the array 100 will decrease the tangential angle β, for element B by β2, and increase the tangential angle α for element A by α2. One of ordinary skill in the art would appreciate that by concaving the array 100, elements A and B will have the most significant impact on the resulting beam 120 as compared to any imaging elements in between elements A and B, and the center imaging elements will be least affected.

The following is an approach to calculating the radius of curvature R of a concave phased array 100 that enables the tangential angles α and β, to be equal at the maximum azimuthal direction θ. From FIG. 2, the following is true:

$$\alpha = \alpha 1 + \alpha 2, \quad (1)$$

and $$\beta = \beta 1 - \beta 2 \quad (2)$$

and because of geometric symmetry, we have:

$$\alpha 2 = \beta 2 = \alpha 3, \quad (3)$$

To obtain α=β, the following is deduced:

$$\alpha 1 + \alpha 3 = \beta 1 - \alpha 3, \quad (4)$$

which means:

$$\alpha 3 = (\beta 1 - \alpha 1)/2, \quad (5)$$

Since:

$$\sin(\alpha 3) = (L/2)/R \quad (6)$$

and:

$$\tan(\alpha 1) = OF \cos(\theta)/(OF \sin(\theta) + L/2) \quad (7)$$

and:

$$\tan(\beta 1) = OF \cos(\theta)/(OF \sin(\theta) - L/2) \quad (8).$$

Combining equations (5)-(8), the radius of curvature R can be expressed as:

$$R = \frac{L/2}{\sin\left(\frac{\tan^{-1}\left(\frac{OF\cos\theta}{OF\sin\theta - L/2}\right) - \tan^{-1}\left(\frac{OF\cos\theta}{OF\sin\theta + L/2}\right)}{2}\right)} \quad (9)$$

In the case of a 10 MHz, 64 element phased array, wherein the length of the array is 5 mm, if the array's maximum angle in the azimuthal direction is 45°, and the focal depth is 5 mm, then the radius of curvature R is preferably approximately 7 mm.

Equation (9) expresses the radius of curvature of a concave array, R, as a function of a desired focal depth if the other parameters in the array design, such as image range, have been provided. For an image range from OF1 to OF2, an average radius of curvature $R_a$ may be determined by:

$$R_a = \int_{OF1}^{OF2} \frac{R(OF)dOF}{OF2 - OF1}. \quad (10)$$

The concave array 100 may have a uniform pitch, wherein the space from element center to element, A and B, is uniform; however, it can be non-uniform as well. An element's width can be varied to maximize the beam quality, as one of ordinary skill in the art would appreciate. For example, the element width can conform to a Gaussian, Bessel, or sinusoidal function using an element index number calculated from the array 100 center to an edge element, e.g., A or B.

For an ultrasound phased array 100, the array 100 can be fabricated by a variety of available active acoustic material, such as piezo-ceramics, piezo-films (thin or thick), 2-2 or 1-3 piezoceramic composites, 2-2 or 1-3 piezocrystal materials, or cMUT. Further, other imaging devices may be used, instead of, or in addition to imaging transducers, such as light based apparatuses for obtaining images through optical coherence tomography (OCT). Image acquisition using OCT is described in Huang et al., "Optical Coherence Tomography," Science, 254, Nov. 22, 1991, pp 1178-1181, which is hereby incorporated by reference in its entirety. A type of OCT imaging device, called an optical coherence domain reflectometer (OCDR) is disclosed in Swanson U.S. Pat. No. 5,321,501, which is incorporated herein by reference. The OCDR is capable of electronically performing two- and three-dimensional image scans over an extended longitudinal or depth range with sharp focus and high resolution and sensitivity over the range.

Such an array 100 is useful for intracardiac applications, and may be used for other applications, such as any kind of B-scanner medical applications, ophthalmic ultrasound, HIFU and/or NDT.

Figure 3:
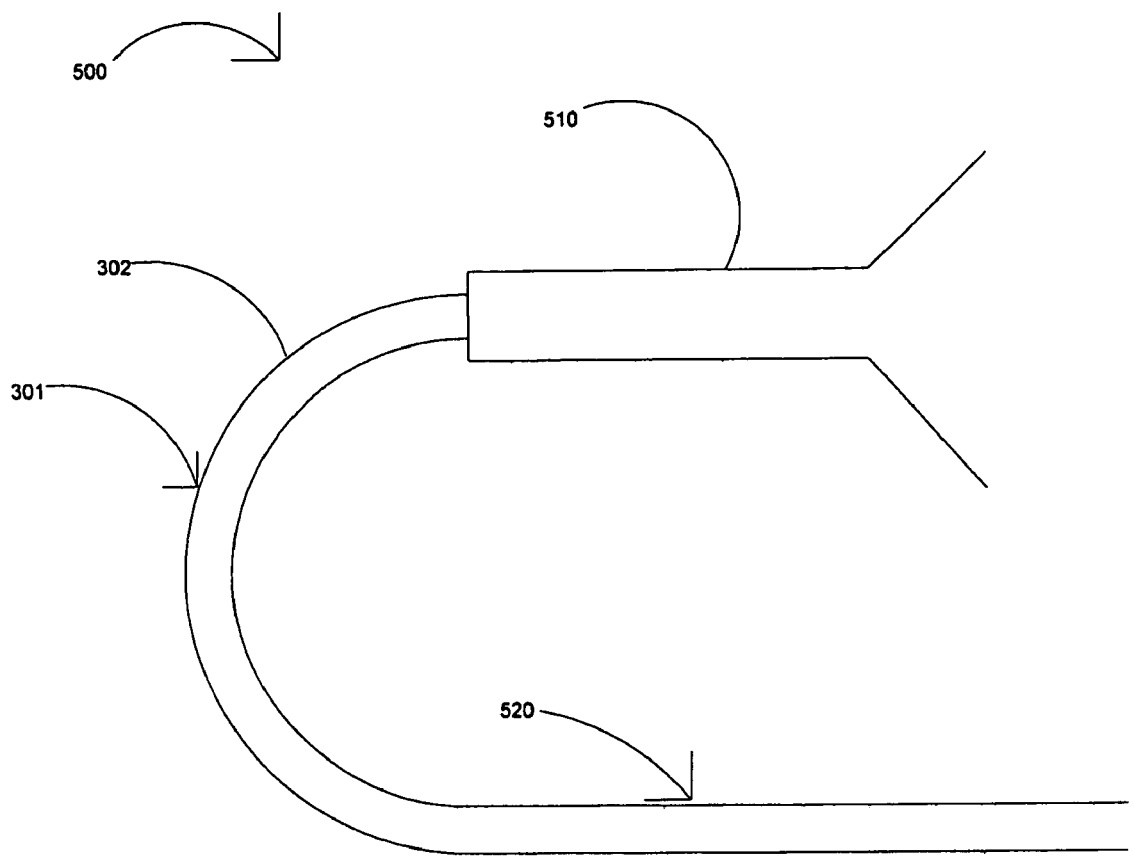
FIG. 3 is a cross-sectional view of an imaging wire in accordance with a preferred embodiment of the present invention.
Figure 4:
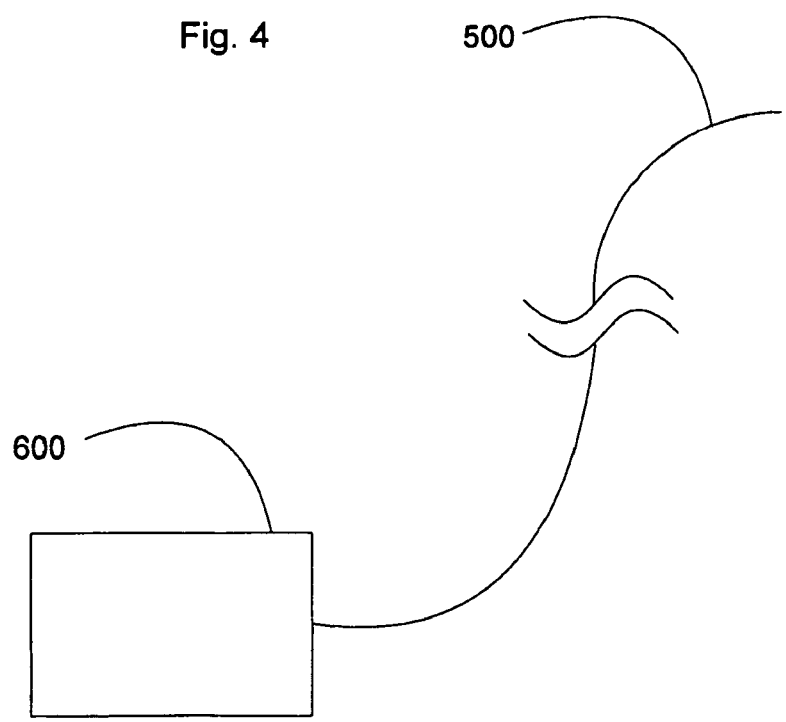
FIG. 4 is a diagram of a medical imaging system in accordance with a preferred embodiment of the present invention.

Turning to FIG. 3, the phased array 100 may be used in a catheter, as described above, and can also be placed in a distal portion 520 of a guidewire 500. The guidewire 500 may comprise a guidewire body 302 in the form of a flexible, elongate tubular member, having an outer wall 301. The guidewire body 302 may be formed of any material known in the art including composite materials, plastics, braided polyimide, polyethylene, PEEK braids, stainless steel, other superelastic materials, or metal alloys, such as a nitinol hypertube, Turning to FIG. 4, a proximal portion 510 of the guidewire 500, shown in FIG. 3, may be adapted to connect to circuitry 600 that processes imaging signals from the phased array 100, such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An intravascular device comprising:
   a catheter having proximal and distal portions; and
   a phased array of imaging elements, including edge elements on opposite ends of the phased array, the edge elements each having an angle of emission, located in the distal portion of the catheter, wherein the phased array is concave having a radius of curvature such that the phased array is steered and focused to a focal point in a maximal azimuthal direction, the angles of emission of the edge elements are substantially similar, wherein the phased array defines an x-axis that extends through midpoints of the edge elements, and wherein the focal point is positioned such that a projection of the focal point onto the x-axis is to a same side of each of the edge elements.

2. The intravascular device of claim 1, wherein the imaging elements are ultrasound imaging transducers.

3. The intravascular device of claim 1, wherein the imaging elements are optical coherence tomography imaging elements.

4. The intravascular device of claim 1, wherein the phased array has a uniform pitch.

5. The intravascular device of claim 1, wherein the phased array has a non-uniform pitch.

6. The intravascular device of claim 1, wherein the width of each imaging element conforms to one of a Gaussian function, a Bessel function, or a sinusoidal function.

7. The intravascular device of claim 1, wherein the phased array is substantially concave.

8. The intravascular device of claim 2, wherein each of the ultrasound imaging transducers comprises an acoustic lens coupled with a layer of piezoelectric crystal, the piezoelectric crystal being coupled with a backing material.

9. A medical imaging system comprising:
   a guidewire having proximal and distal portions;
   a concave phased array of imaging elements located in the distal portion of the guidewire, the imaging elements including edge elements on opposite ends of the phased array, the edge elements each having an angle of emission, wherein the phased array has a radius of curvature such that the phased array is steered and focused to a focal point in a maximal azimuthal direction, the angles of emission of the edge elements are substantially similar, wherein the phased array defines an x-axis that extends through midpoints of the edge elements, and wherein the focal point is positioned such that a projection of the focal point onto the x-axis is to a same side of each of the edge elements; and
   an image processing device coupled to the proximal portion of the guidewire.

10. The medical imaging system of claim 9, wherein the imaging elements are ultrasound imaging transducers.

11. The medical imaging system of claim 9, wherein the imaging elements are optical coherence tomography imaging elements.

12. The medical imaging system of claim 9, wherein the phased array has a uniform pitch.

13. The medical imaging system of claim 9, wherein the phased array has a non-uniform pitch.

14. The medical imaging system of claim 9, wherein the width of each imaging element conforms to one of a Gaussian function, a Bessel function, or a sinusoidal function.

15. The medical imaging system of claim 9, wherein the concaved phased array is substantially concave.

16. The medical imaging system of claim 10, wherein each of the ultrasound imaging transducers comprises an acoustic lens coupled with a layer of piezoelectric crystal, the piezoelectric crystal being coupled with a backing material.

17. A method of medical imaging, comprising the steps of:
   advancing an imaging catheter, having a distal section, into an area of interest within a vessel of a patient, wherein the distal section of the imaging catheter includes a concaved phased array of imaging elements;
   steering the phased array in a maximal azimuthal direction, wherein the phased array of imaging elements includes edge elements on opposite ends of the phased array, the edge elements each having an angle of emission, wherein the phased array has a radius of curvature such that when the phased array is steered in a maximal azimuthal direction, the angles of emission of the edge elements are substantially similar, and wherein the phased array defines an x-axis that extends through midpoints of the edge elements;
   focusing the phased array at a focal point in the maximal azimuthal direction, wherein the focal point is positioned such that a projection of the focal point onto the x-axis is to a same side of each of the edge elements; and
   imaging the area of interest.

18. The method of claim 17, wherein the concaved phased array is substantially concave.

19. The method of claim 17, wherein the imaging elements are ultrasound imaging transducers.

20. The method of claim 17, wherein the imaging elements are optical coherence tomography imaging elements.

21. The method of claim 17, wherein the phased array has a uniform pitch.

22. The method of claim 17, wherein the phased array has a non-uniform pitch.

* * * * *

UNITED STATES PATENT AND TRADEMARK OFFICE
CERTIFICATE OF CORRECTION

PATENT NO. : 7,625,343 B2  Page 1 of 1
APPLICATION NO. : 11/173550
DATED : December 1, 2009
INVENTOR(S) : Cao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 777 days.

Signed and Sealed this

Twenty-sixth Day of October, 2010

David J. Kappos
*Director of the United States Patent and Trademark Office*